United States Patent [19]

Buckwalter et al.

[11] Patent Number: 5,030,650

[45] Date of Patent: Jul. 9, 1991

[54] 13-HALO-23-IMINO DERIVATIVES OF LL-F28249 COMPOUNDS AND THEIR USE AS ENDO- AND ECTOPARASITICIDAL, INSECTICIDAL, ACARICIDAL AND NEMATOCIDAL AGENTS

[75] Inventors: Brian L. Buckwalter, Yardley, Pa.; Shin-Shyong Tseng, Bridgewater, N.J.

[73] Assignee: American Cyanamid Company, Stamford, Conn.

[21] Appl. No.: 405,808

[22] Filed: Sep. 11, 1989

[51] Int. Cl.$^5$ .................. A01N 43/58; C07D 305/00; C07D 316/06

[52] U.S. Cl. ..................................... 514/450; 549/264; 549/268

[58] Field of Search ................. 549/264, 268; 514/450

[56] References Cited

U.S. PATENT DOCUMENTS

| | | | |
|---|---|---|---|
| 4,134,973 | 1/1979 | Fisher et al. | 549/264 |
| 4,173,571 | 11/1979 | Chabala et al. | 549/264 |
| 4,228,079 | 10/1980 | Calton | 549/268 |
| 4,587,247 | 5/1986 | Linn et al. | 549/264 |
| 4,696,922 | 9/1987 | Sturm et al. | 549/264 |
| 4,806,527 | 2/1989 | Christensen et al. | 549/264 |

FOREIGN PATENT DOCUMENTS

| | | | |
|---|---|---|---|
| 0170006 | 2/1986 | European Pat. Off. | 549/264 |
| 0203832 | 12/1986 | European Pat. Off. | 549/264 |

OTHER PUBLICATIONS

Sankyo Co. Ltd., Abstract JO 1056-681-A dated Aug. 25, 1987. Macrolide Compounds obtained from milbemycin.

Primary Examiner—Mary C. Lee
Assistant Examiner—Robert C. Whittenbaugh
Attorney, Agent, or Firm—Carmella A. O'Gorman

[57] ABSTRACT

There are provided certain 13-halo-23-imino-LL-F28249 compounds which are useful for controlling endo- and ectoparasites, insects, acarids and nematodes.

13 Claims, No Drawings

13-HALO-23-IMINO DERIVATIVES OF LL-F28249 COMPOUNDS AND THEIR USE AS ENDO- AND ECTOPARASITICIDAL, INSECTICIDAL, ACARICIDAL AND NEMATOCIDAL AGENTS

SUMMARY OF THE INVENTION

The present invention relates to certain 13-halo-23-imino-LL-F28249 compounds and their use for controlling endo- and ectoparasitic infections in warm-blooded animals and controlling insect, acarid and nematode infestations in agricultural crops and controlling the housefly.

The designation LL-F28249 is used to describe compounds produced by the fermentation broth of *Streptomyces cyaneogriseus*, subspecies noncyanogenus, deposited in the NRRL collection under deposit accession number 15773. The morphological characteristics of said compounds and methods for the production thereof are described in U.S. Pat. No. 4,869,901, which is incorporated herein by reference.

DESCRIPTION OF THE PREFERRED EMBODIMENTS

The compounds of the invention have the structural formula:

wherein
$R_1$ is methyl, ethyl or isopropyl;
$R_7$ is hydrogen and $R_8$ is $OR_2$, or when taken together with the carbon atom to which they are attached $R_7$ and $R_8$ represent C=O;
$R_2$ is hydrogen, $C_1$-$C_4$ alkyl, or $$\overset{O}{\underset{\|}{C}}-R_4;$$

$R_4$ is hydrogen, $C_1$-$C_4$ alkyl, $C_1$-$C_4$ haloalkyl, $C_1$-$C_4$ alkoxy, phenoxy, $C_1$-$C_4$ alkoxymethyl, phenoxymethyl, or phenyl optionally substituted with 1 nitro, 1-3 halogens, 1-3 $C_1$-$C_4$ alkyl, or 1-3 $C_1$-$C_4$ alkoxy;
$R_3$ is hydrogen, methyl or ethyl;
X is fluorine, bromine, chlorine or iodine;
W is oxygen or N=Y;
Y is $OR_5$ or $NHR_6$;
$R_5$ is $C_1$-$C_4$ alkyl or $C_1$-$C_4$ acyl; and
$R_6$ is $C_1$-$C_4$ acyl; and the dotted triangular figure with oxygen at $C_{26}$-$C_{27}$ indicates that there is present either a double bond or an epoxide.

A preferred group of 13-halo-23-imino-LL-F28249 compounds have the structural formula shown above wherein
$R_1$ is isopropyl;
$R_7$ is hydrogen and $R_8$ is $OR_2$;
$R_2$ is hydrogen, $C_1$-$C_4$ alkyl, or $$\overset{O}{\underset{\|}{C}}-R_4;$$

$R_4$ is hydrogen, methyl, chloromethyl, dichloromethyl, trichloromethyl, or methoxymethyl;
$R_3$ is methyl;
X is fluorine;
W is N=Y;
Y is $OR_5$; and
$R_5$ is $C_1$-$C_4$ alkyl.

The compounds of the invention are effective antiendoparasitic and antiectoparasitic agents and can be used to protect warm-blooded animals against infestations of the above-said pests. They may also be applied to a wide variety of agronomic crops and the surroundings in which said crops are grown or growing to protect said crops from the damage caused by insects, acarids and nematodes. They are highly effective for the control of the housefly when applied to the habitat, food source, or breeding ground of the housefly.

The LL-F28249 comounds are represented by the following structural formula:

| Component | $R_1$ | $R_2$ | $R_3$ | $R_7$ |
|---|---|---|---|---|
| LL-F28249α | $CH(CH_3)_2$ | H | $CH_3$ | $CH_3$ |
| LL-F28249β | $CH_3$ | H | $CH_3$ | $CH_3$ |
| LL-F28249γ | $CH_3$ | $CH_3$ | $CH_3$ | $CH_3$ |
| LL-F28249ε | $CH(CH_3)_2$ | H | H | $CH_3$ |
| LL-F28249ζ | $CH_2CH_3$ | H | $CH_3$ | $CH_3$ |
| LL-F28249θ | $CH(CH_3)_2$ | H | $CH_3$ | $CH_2CH_3$ |
| LL-F28249ι | $CH(CH_3)_2$ | H | $CH_2CH_3$ | $CH_3$ |
| LL-F28249λ | $CH(CH_3)_2$ | $CH_3$ | $CH_3$ | $CH_3$ |

Surprisingly, it has been found that chemical modification at the 5, 13, 23, 26 and 27 positions of the LL-F28249 compounds shown above enhances the endoand ectoparisiticidal, insecticidal, acaricidal and nematocidal activity of said compounds. More particularly, the 13-halo-23-imino derivatives of 5-hydroxy and 5-o-substituted-LL-F28249 and 26,27-epoxy-LL-F28249 compounds demonstrate potent endectocidal and insecticidal activity.

Functionalization at the 13 position of the above shown LL-F28249 compounds is achieved by oxidation of the 5 and 23 hydroxy groups with pyridinium dichromate in dimethylformamide to give the 5,23-dioxo-LL-F28249 compound (I) followed by reaction with selenium dioxide and formic acid to give the 13-(formyloxy)-5,23-dioxo-F28249 compound (II). The thus-obtained compound (II) is converted to the 13-hydroxy-5,23-dioxo-LL-F28249 compound (III) via acid hydrolysis and then reacted with diamino sulfur trifluoride (DAST) to give the 13-fluoro-5,23-dioxo-LL-F28249 compound (IV). Compound (IV) is reacted sequentially with methoxylamine hydrochloride and sodium borohydride to give the 13-fluoro-23-methoximino-LL-F28249 compound (VI). Using LL-F28249α as the starting material, the above-described reaction sequence is illustrated in Flow Diagram I shown below.

FLOW DIAGRAM I

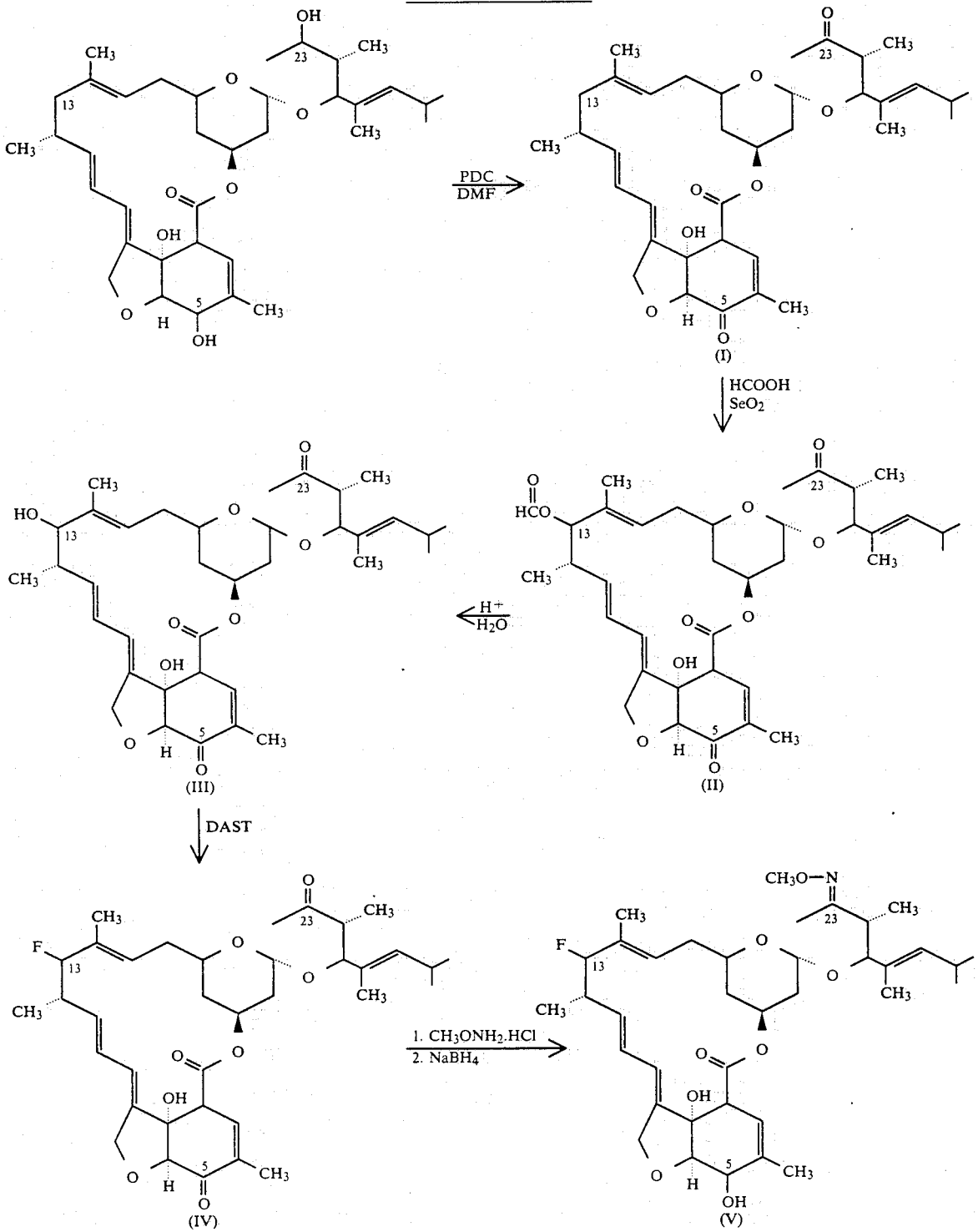

Compound (III) is used as a common intermediate and reacted with halogenating reagents such as phosphorous tribromide and thionyl chloride to give the 13-bromo- or 13-chloro- or 13-iodo-5,23-dioxo-LL-F28249 compounds represented by compound (IV)

Derivatization of the 5-hydroxy moiety to give novel 5-alkyloxy and 5-acyloxy-13-halo-23-imino-LL-F28249 compounds is achieved by reacting compound (VI) with an alkylating or acylating agent as illustrated in Flow Diagram II.

FLOW DIAGRAM II

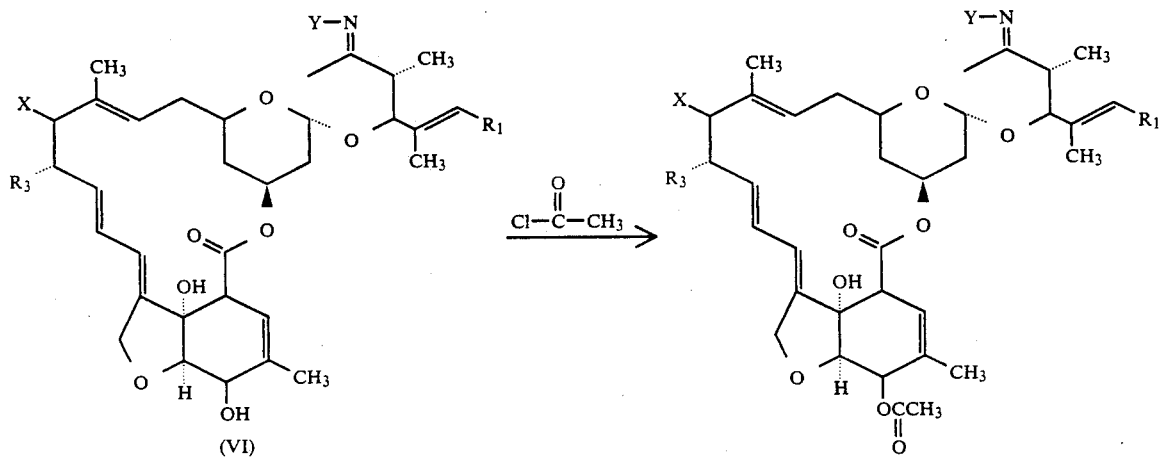

wherein F is Br or Cl or I, and then reacted sequentially with an alkoxyamine, or hydroxylamine, and sodium borohydride to give the corresponding 13-halo-23-imino-LL-F28249 compounds represented by compound (V) wherein F is Br or Cl or I as shown in Flow Diagram I, above.

$R_1$, $R_3$, X and Y are as described hereinabove.

Alternatively, compounds of the invention are prepared by reacting the LL-F28249 starting material with an acyl halide such as p-nitrobenzoylchloride followed by oxidation of the 23-hydroxy group and functionalization at the 13 carbon to give the intermediate compound (VII) as illustrated in Flow Diagram III.

FLOW DIAGRAM III

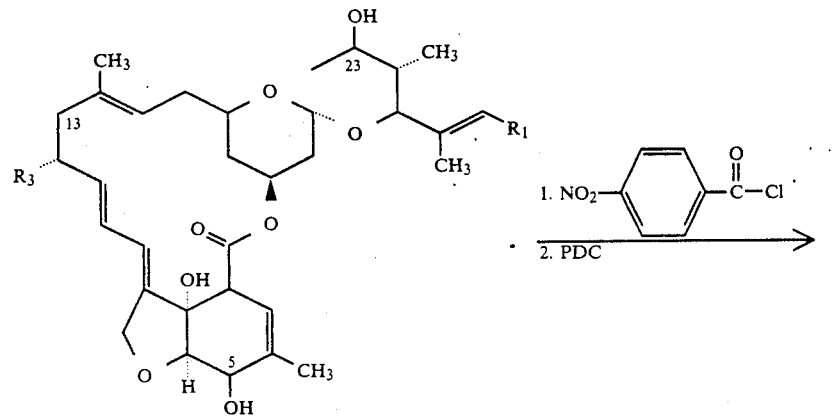

FLOW DIAGRAM III

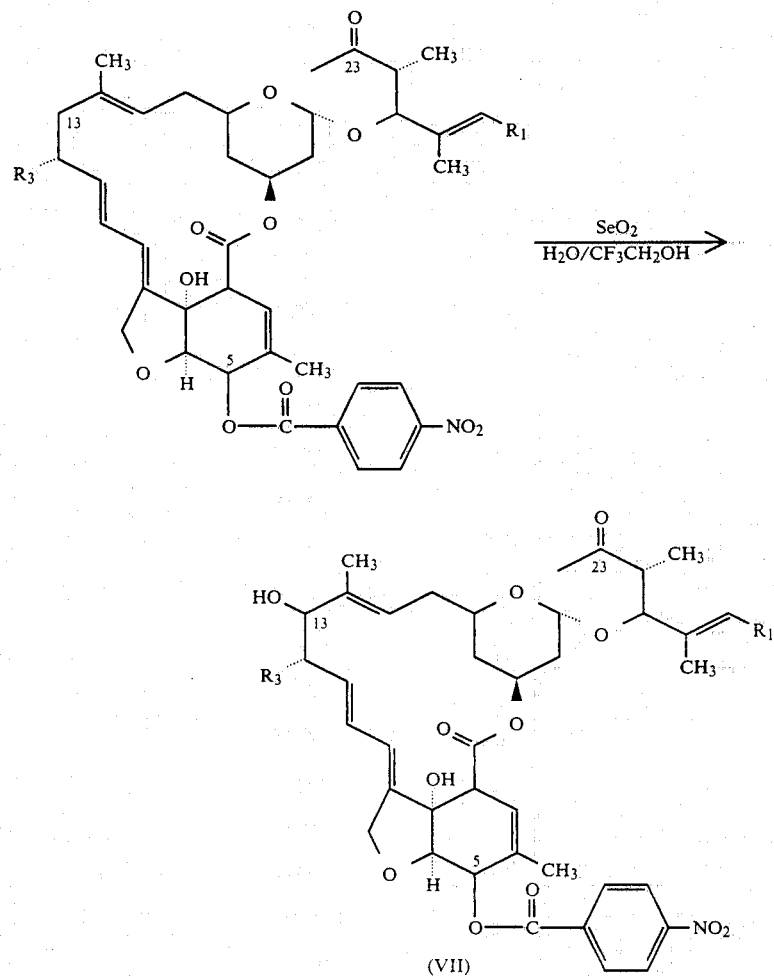

Compound (VII) is treated with an halogenating agent such as diamino sulfur trifluoride, thionyl chloride or phosphorous tribromide followed by reaction with an alkoxyl or hydroxylamine to give the desired 13-halo-23-imino-5-(acyloxy)-LL-F28249 compounds such as compound (VIII). Optionally, compound (VIII) is hydrolyzed in base to give the corresponding 13-halo-23-imino-LL-F28249 compounds. The reaction sequence is illustrated in Flow Diagram IV.

FLOW DIAGRAM IV

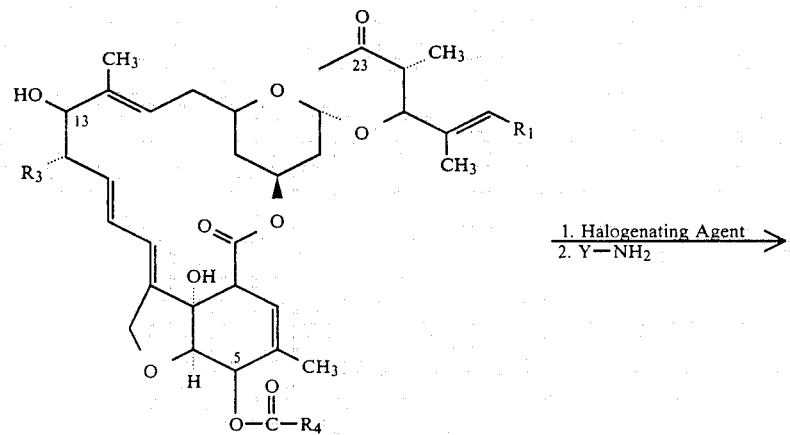

-continued

FLOW DIAGRAM IV

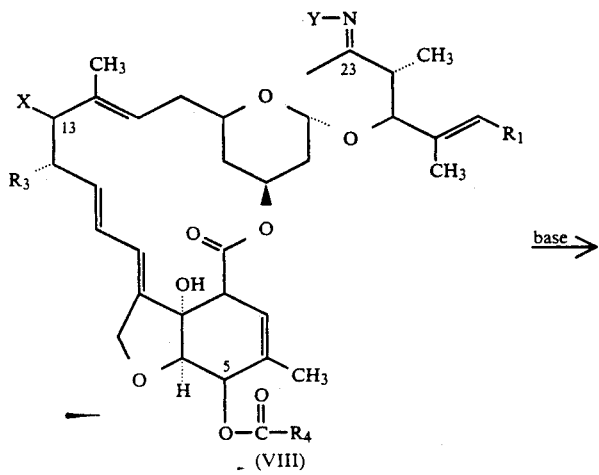

(VIII)

base →

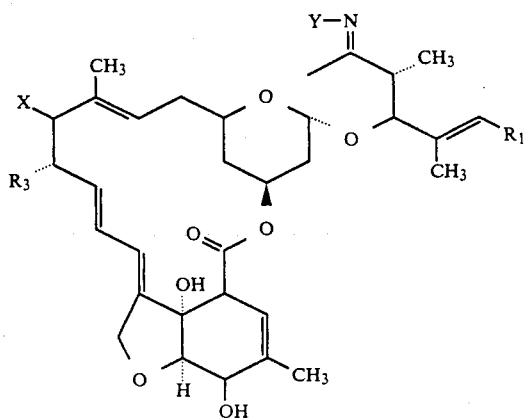

$R_1$, $R_3$, $R_4$, X and Y are as described hereinabove.

Advantageously, the 26,27 epoxide derivatives of 13-halo-23-imino-LL-F28249 compounds are prepared by reacting the 13-halo-23-oxo precursor with m-chloroperbenzoic acid followed by treatment of the 26,27 epoxide product with an alkoxyl, acyloxyl or hydroxyloxime to give the desired compounds (IX) as illustrated in Flow Diagram V.

FLOW DIAGRAM V

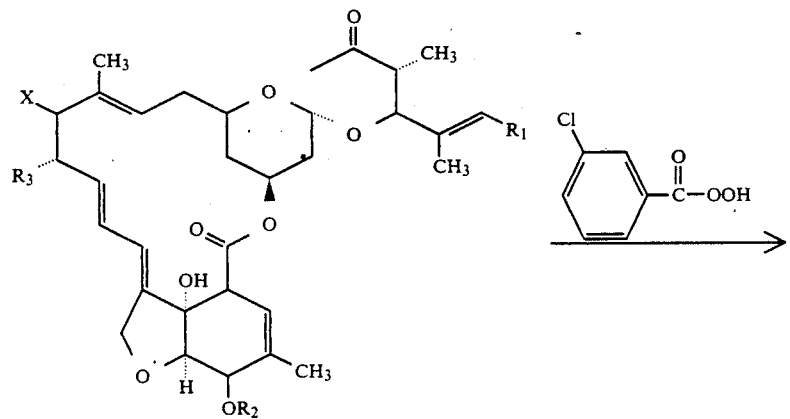

FLOW DIAGRAM V -continued

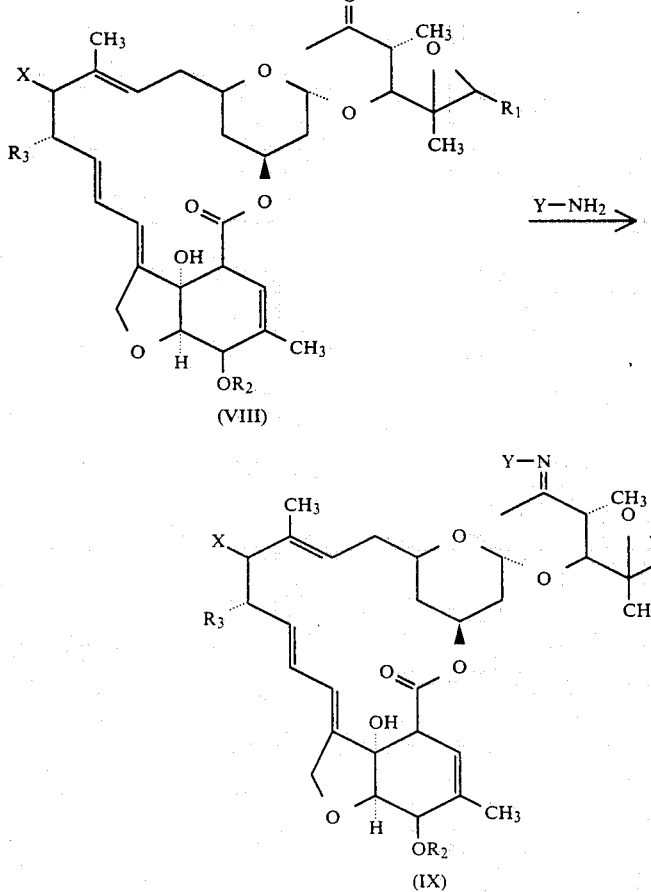

$R_1$, $R_2$, $R_3$, X and Y are as described hereinabove.

Surprisingly, it has been found that the compounds of the invention are highly effective endo and ectoparasiticidal agents useful for treating warm-blooded animals. It has also been found that said compounds are excellent insecticidal, nematicidal and acaricidal agents useful for controlling said pests and protecting agronomic crops from damage caused by said pests.

For use in the treatment of warm-blooded animals such as cattle, sheep, swine, horses, dogs or other mammals, the compounds of the invention may be administered orally in a dosage unit form such as a capsule, bolus or tablet, or as a liquid drench. The drench is normally a solution, suspension or dispersion of the active ingredient usually in water together with a suspending agent such as bentonite and a wetting agent or like excipient and an antifoaming agent. Drench formulations generally contain from about 0.001 to 0.5% by weight of the active compound. The capsules and boluses comprise the active ingredient admixed with a carrier vehicle such as starch, talc, magnesium stearate or di-calcium phosphate.

Where it is desired to administer the LL-F28249 derivatives in a dry, solid dosage unit form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such dosage unit formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of the invention may be administered to animals parenterally, for example, by intraruminal, intramuscular, intratracheal, or by subcutaneous injection, in which event the active ingredient is dissolved or dispersed in a liquid carrier vehicle. For parenteral administration, the active material is admixed with an acceptable vehicle, preferably a vegetable oil such as peanut oil, cotton seed oil or the like. Other parenteral vehicles such as organic preparations using solketal, propylene glycol, glycerol formal and aqueous parenteral compositions may also be used in the preparation of parenteral formulations for administration to warm-blooded animals.

In these formulations the active compound or compounds are dissolved or suspended in the formulation in sufficient amount to provide from about 0.005% to 5% by weight of the active compound in said formulation.

The compounds of the invention are useful for treating endoparasites in warm-blooded animals such as helminths. Said compounds are also useful for the prevention and treatment of diseases caused by ectoparasites, for example, arthopod ectoparasites such as mites, ticks, lice, fleas and other biting insects in domesticated animals and poultry.

Further, the 13-halo-23-imino-LL-F28249 compounds described herein are excellent insecticidal, nematicidal and acaricidal agents useful for protecting, growing or harvested crops from attack by the abovesaid pests. The compounds of the invention may be formulated into dry compacted granules, flowable compositions, wettable powders, dusts, dust concentrates, microemulsions and the like, all of which lend themselves to soil, water and/or foliage application and provide the requisite plant protection. Such compositions include the compounds of the invention admixed with agronomically acceptable solid or liquid carriers.

In these compositions the active compounds are intimately mixed or ground together with the composition in sufficient amounts to provide from 3% to 20% by weight of the active compound in said composition.

The compositions of this invention are useful in combating agricultural pests that inflict damage upon crops while they are growing or while in storage. The compounds are applied using known techniques such as sprays, dusts, emulsions, wettable powders, flowables and the like to the growing or stored crops to provide protection against infestation by agricultural pests.

Still further, compounds of this invention are outstandingly effective for controlling pupation of housefly larvae thereby being useful in the control of the housefly in the habitat, food source or breeding ground of said housefly. The compounds can be applied using sprays, dusts, emulsions, wettable powders, flowables, microemulsion granular compositions and the like as described hereinabove to said habitat, food source or breeding ground of said housefly.

In order to facilitate a further understanding of the invention, the following examples are presented primarily for the purpose of illustrating certain more specific details thereof. The invention is not to be limited thereby except as defined in the claims.

Unless otherwise noted, all parts are by weight.

EXAMPLE 1

Preparation of 5,23-dioxo-LL-F28249α

A mixture of LL-F28249α (10.0 g, 0.016 mole) and diatomaceous earth (160.0 g) in dimethylformamide, under nitrogen, is treated portionwise with pyridinium dichromate (58.0 g, 0.15 mole), stirred for 4 hours at room temperature, treated with 1 L of diethyl ether, stirred for 15 minutes and filtered. The filtrate is washed with water followed by brine, dried over $MgSO_4$ and concentrated in vacuo to give a yellow oil residue. The residue is flash chromatographed (silica, methylene chloride:isopropanol 99:1 as eluent) to afford the title product as a light yellow solid (4.84 g, 49.7%), identified by $^1$HNMR, $^{13}$CNMR and mass spectral analyses.

EXAMPLE 2

Preparation of 13-(formyloxy)-5,23-dioxo-LL-F28249α

A mixture of 5,23-dioxo-LL-F28249α (2.6 g, 4.3 mmole) in 88% formic acid, under nitrogen, is treated with selenium dioxide (1.0 g, 9.0 mmole), stirred at 50° for 2 hours, cooled to room temperature, treated with 3 volumes of methylene chloride, stirred for 10 minutes and filtered through diatomaceous earth. The filtrate is separated and the organic phase is concentrated in vacuo to give a light brown solid residue. Flash column chromatography (silica, hexanes:ethyl acetate, 2:1 as eluent) of the residue affords the title product as a beige solid (1.3 g, 43%), identified by $^1$HNMR and $^{13}$CNMR spectroscopy.

EXAMPLE 3

Preparation of 13-hydroxy-5,23-dioxo-LL-F28249α

A mixture of 13-(formyloxy)-5,23-dioxo-LL-F28249α (800 mg, 1.1 mmole), methanol and dioxane, at 0°–5° C. is treated with 20 mL of 1.2N HCl, stirred at room temperature for 4 hours, allowed to stand at 40° C. for 16 hours and concentrated in vacuo. The residue is taken up in ethyl acetate, washed with sodium bicarbonate solution followed by brine, dried over $MgSO_4$ and concentrated in vacuo, to give the title compound as a beige solid (700 mg, 91%), identified by $^1$HNMR, $^{13}$CNMR and mass spectral analyses.

EXAMPLE 4

Preparation of 13-fluoro-5,23-dioxo-LL-F28249α and 13-fluoro-23-oxo-LL-F28249α

A mixture of 13-hydroxy-5,23-dioxo-LL-F28249α (100 mg, 0.15 mmole) in methylene chloride at −40° C., under nitrogen, is treated with dimethylaminosulfur trifluoride (40 μl, 29.4 mg, 0.22 mmole) via a syringe and stirred at −40° C. to −30° C. for 3 hours. The reaction mixture is poured into ice water, and the phases are separated. The aqueous phase is extracted with ethyl acetate. The organic phases are combined, washed with water and brine, dried over $MgSO_4$ and concentrated in vacuo to give the title product mixture as a yellow solid, 112 mg. High pressure liquid chromatography (HPLC) analysis indicates 57% 13-fluoro-5,23-dioxo-LL-F28249α and 13% 13-fluoro-23-oxo-LL-F28249α is present in the mixture. Column chromatography (silica, hexanes:ethyl acetate, 4:1 as eluent) of the product mixture affords pure 13-fluoro-5,23-dioxo-LL-F28249α as a yellow solid, identified by $^1$H, $^{13}$C and $^{19}$F NMR and mass spectral analyses.

EXAMPLE 5

Preparation of 13-fluoro-23-(O-methyloxime)-LL-F28249α

A mixture of 13-fluoro-5,23-dioxo-LL-F28249α (30 mg, 0.05 mmole) in absolute ethanol at −10° C. to −5° C., under nitrogen, is treated with imidazole (10 mg, 0.15 mmole) followed by addition of methoxylamine hydrochloride (12.5 mg, 0.15 mmole), stirred for 2 hours at −10° C. to −5° C., treated with sodium borohydride (12.0 mg, 0.30 mmole) and stirred for 1 hour at −10° C. to −5° C. The reaction mixture is quenched with water, stirred for 15 minutes at ambient temperatures and concentrated in vacuo. The resultant residue is dispersed in ethyl acetate and water, the phases are separated and the organic phase is washed with water followed by brine, dried over $MgSO_4$ and concentrated in vacuo to give a residue. The residue is column chromatographed (silica, hexanes: ether, 4:1 as eluent) to afford the title product as a white solid, identified by $^1$H, $^{13}$C and $^{19}$F NMR and mass spectral analysis.

EXAMPLE 6

Preparation of 13-fluoro-5-(formyloxy)-23-(O-methyloxime)-LL-F28249α

A mixture of 13-fluoro-23-(O-methyloxime)-LL-F28249α (80 mg, 0.12 mmole) in dry pyridine at 0° C., under nitrogen, is treated with 1.0 mL of the mixed anhydride of acetic acid and formic acid, stirred at room temperature for ½ hour then poured onto a mixture of ice and saturated sodium bicarbonate solution. The reaction mixture is extracted with ether, the ether extract is washed with cold dilute hydrochloric acid solution, followed by a water wash and a saturated sodium bicarbonate wash. The organic phase is dried over $Na_2SO_4$ and concentrated in vacuo. The resultant residue is flash chromatographed (silica, methylene chloride:ethyl acetate, 40:1 as eluent) to afford the title product as a white solid (34.4 mg, 42%) identified by $^1H$ and $^{13}C$ NMR and mass spectral analyses.

EXAMPLE 7

Preparation of 5-(dichloroacetoxy)-13-fluoro-23-(O-methyloxime)-LL-F28249α

A stirred mixture of 13-fluoro-23-(O-methyloxime)-LL-F28249α (85 mg, 0.12 mmole) and dimethylaminopyridine (2.9 mg, 0.024 mmole) in methylene chloride at 5°-10° C., under nitrogen, is treated with pyridine (50 μL, 0.62 mmole) followed by dichloroacetyl chloride (0.02 μL, 0.208 mmole). After 2 hours at 5°-10° C., the reaction mixture is poured onto saturated sodium bicarbonate and ice and extracted with ether. The organic phase is washed sequentially with dilute (0.5%) hydrochloric acid, water and saturated sodium bicarbonate solution, dried over $Na_2SO_4$ and concentrated in vacuo. The residue is flash chromatographed (silica, 0.25% to 0.5% isopropanol in methylene chloride, gradient elution) to give the title product as a white solid, identified by $^1H$ and $^{13}C$ NMR and mass spectral analyses.

EXAMPLE 8

Preparation of 13-fluoro-23-(O-methyloxime)-5-(trichloroacetoxy)-LL-F28249α

A stirred mixture of 13-fluoro-23-(O-methyloxime)-LL-F28249α (80 mg, 0.12 mmole) and dimethylaminopyridine (2.9 mg, 0.024 mmole) in methylene chloride, at 5°-10° C. under nitrogen, is treated with pyridine (50 μL, 0.62 mmole) followed by trichloroacetyl chloride (20 μL, 0.18 mmole). After 1½ hours at 5°-10° C., the reaction mixture is poured into saturated sodium bicarbonate and ice and extracted with ether. The organic phase is washed sequentially with dilute (0.5%) hydrochloric acid, water and saturated sodium bicarbonate, dried over $Na_2SO_4$ and concentrated in vacuo to give a white foam residue. The residue is flash chromatographed (silica, 0.10% to 0.25% isopropanol in methylene chloride, gradient elution) to afford the title product as an off-white solid (63.4 mg, 66%) identified by $^1H$ and $^{13}C$ NMR and mass spectral analyses.

EXAMPLE 9

Preparation of 5-[(p-nitrobenzoyl)oxy]-LL-F28249α

A mixture of LL-F28249α (6.36 g, 10.4 mmole) and pyridine (1.98 g, 25 mmole) in methylene chloride at 20°-25° C. is treated with p-nitrobenzoyl chloride (2.45 g, 13.2 mmole), stirred for 4 hours, allowed to stand for 16 hours and treated with saturated sodium bicarbonate and methylene chloride. The reaction mixture is stirred for 5 minutes and the phases are separated. The organic phase is washed sequentially with saturated sodium bicarbonate, 5% hydrochloric acid and brine, dried over $MgSO_4$ and concentrated in vacuo to afford the title product as a white solid foam (7.9 g, 93.5% purity) by liquid chromatography analysis) identified by $^1HNMR$ and mass spectral analyses and microanalysis.

EXAMPLE 10

Preparation of 5-[(p-nitrobenzoyl)oxy]-23-oxo-LL-F28249α

A stirred mixture of 5-[(p-nitrobenzoyl)-oxy]-LL-F28249α (6.3 g, 8.4 mmole) in dimethylformamide is treated with pyridinium dichromate all at once at 20°-25° C. The reaction mixture is stirred for 6 hours, poured into water, stirred for 15 minutes and filtered. The filter cake is washed with water, air-dried, taken up in refluxing ethyl acetate, treated with diatomaceous earth and filtered. The filtrate is concentrated in vacuo to give a red-brown solid residue. The residue is recrystallized from n-propanol to afford the title product as white crystals (3.3 g, 51.7%) identified by $^1HNMR$ and mass spectral analyses.

EXAMPLE 11

Preparation of 13-hydroxy-5-[(p-nitrobenzoyl)oxy]-23-oxo-LL-F28249α

A stirred mixture of 5-[(p-nitrobenzoyl)-oxy-]-23-oxo-LL-F28249α (1.25 g, 1.36 mmole) and selenium dioxide (0.78 g, 7.02 mmol) in 20 mL of 9:1 trifluoroethanol:water is heated at 40° C. for 4 hours, cooled to room temperature and filtered through diatomaceous earth. The filtrate is concentrated in vacuo; the resultant residue is taken up in methylene chloride and filtered to remove any residual selenium dioxide and the filtrate is concentrated in vacuo; the resultant residue is flash chromatographed (silica ethyl acetate:hexanes 1:2 as eluent) to afford the title product as a white solid (0.29 g, 27%) identified by $^1H$ and $^{13}CNMR$ and mass spectral analyses.

EXAMPLE 12

Preparation of 13-fluoro-5-[(p-nitrobenzoyl)oxyl]-23-oxo-LL-F28249α

A mixture of 13-hydroxy-5-[(p-nitrobenzoyl)-oxy]-23-oxo-LL-F28249α (0.5 mmole) in dry methylene chloride, under nitrogen, at −70° C. is treated dripwise with dimethylamino sulfur trifluoride (80 μl, 0.60-mmole) via a syringe. After 20 minutes at −70° C., the reaction mixture is quenched with ½ mL of water and 1 mL of methanol and stirred for 15 minutes at −78° C. to 0° C., allowed to warm to room temperature and concentrated in vacuo. The residue is flash chromatographed (silica, methylene chloride/ethyl acetate mixtures as eluent) to afford the title product as a white solid (236 mg, 58.7%) identified by $^1H$, $^{13}C$ and APT NMR and mass spectral analyses.

EXAMPLE 13

Preparation of 13-fluoro-23-oxo-LL-F28249α

A rapidly stirred mixture of 13-fluoro-5-[(p-nitrobenzoyl)oxy]-23-oxo-LL-F28249α (187 mg, 0.24 mmole) in dioxane at 5° C. is treated dropwise with 1N NaOH (0.35 mL, 0.35 mmol), stirred at 10°–15° C. for 3 hours, diluted with ethyl acetate and water, and mixed well. The phases are separated and the organic phase is washed with water, dried over NaSO$_4$ and concentrated in vacuo. The residue is flash chromatographed (silica, ethyl acetate:hexane, 1:2–1:1 gradient elution) to give the title product as a white powder (117 mg, 78%), identified by $^1$H and $^{13}$CNMR and mass spectral analyses.

EXAMPLE 14

Preparation of 26,27-epoxy-13-fluoro-23-oxo-LL-F28249α (I) and 3,4:26,27-diepoxy-13-fluoro-23-oxo-LL-F28249α (II)

A stirred mixture of 13-fluoro-23-oxo-L-L-F28249α (62.8 mg, 0.10 mmole) in methylene chloride at 5°–10° C. is treated with purified m-chloroperbenzoic acid (41.7 mg, 0.24 mmole), stirred for 3 hours at 5°–10° C. and quenched with 10% sodium bicarbonate solution. The phases are separated and the organic phase is concentrated in vacuo. The resultant residue is flash chromatographed (silica, hexanes:ethyl acetate gradient elution, 2:1–1:1) to give the title product mixture. The mixture is further purified by preparative, reverse phase, high pressure liquid chromatography (HPLC) (C-18 column, acetonitrile:water, 65:35) to afford title product (I) as a white powder (18 mg, 29%) and title product (II) as a white powder (16 mg, 26%). Both compounds (I) and (II) are identified by $^1$H and $^{13}$C NMR and mass spectral analyses.

EXAMPLE 15

Preparation of 26,27-epoxy-13-fluoro-23-(O-methyloxime)-LL-F28249α

A mixture of 26,27-epoxy-13-fluoro-23-oxo-LL-F28249α (7.6 mg, 0.012 mmole), hydroxylamine hydrochloride (4.5 mg, 0.05 mmole) and sodium acetate (6.6 mg, 0.08 mmole) in methanol is stirred at room temperature for 6 hours and concentrated in vacuo. The residue is partitioned between water and methylene chloride. The organic phase is separated and concentrated in vacuo. The resultant residue is chromatographed (silica, ethyl acetate:hexanes, 1:1) to afford the title product as a white powder (6.0 mg, 76%) identified by $^1$H and $^{13}$C NMR and mass spectral analyses.

EXAMPLE 16

Preparation of 13-chloro-5,23-dioxo-LL-F28249α

A mixture of 13-hydroxy-5,23-dioxo-LL-F28249α (70 mg, 0.10 mmole) in methylene chloride, under nitrogen, at 5°–10° C. is treated dripwise with thionyl chloride (30 μL, 18.4 mg, 0.15 mmole) via a syringe, stirred at 5°–10° C. for 2 hours and at room temperature for 16 hours and concentrated in vacuo. The semi-solid residue is flash chromatographed (silica, hexane:ethyl acetate, 75:25) to afford the title product as a beige solid (38.5 mg, 60%) identified by $^1$HNMR and mass spectral analyses.

EXAMPLE 17

Preparation of 13-bromo-5,23-dioxo-LL-F28249α

A mixture of 13-hydroxy-5,23-dioxo-LL-F28249α (97 mg, 0.15 mmole) in benzene, under nitrogen, at 5°–10° C. is treated with phosphorous tribromide (20 μL, 57.6 mg, 0.21 mmole) via a syringe, stirred for 1 hour at 5°–10° C., poured into water and extracted with ethyl acetate. The organic phase is washed with brine, dried over MgSO$_4$, and concentrated in vacuo. The semi-solid residue is chromatographed twice (silica, hexanes:ethyl acetate, 9:1) to afford the title product as a light yellow solid identified by mass spectral analysis.

EXAMPLE 18

Evaluation Of The Antiparasitic Activity Of Test Compounds

The antiparasitic activity of the compounds of the present invention against helminths, acarids, and arthropod ectoparasites at various concentrations of active ingredient is determined by the following test examples. The results of these tests are summarized in Table I.

Evaluation of test compounds for controlling *Trichostrongylus colubriformis* in warm-blooded animals In these tests the active ingredient is dissolved in polyethylene glycol and dimethylsulfoxide (PEG:DMSO) (1:2 v/v) in sufficient quantity to provide treatments that deliver from 0.0156 to 0.1250 mg/kg of test compound to the animal.

To evaluate the test compounds, 5 week old male gerbils are infected with 400–600 infective *T. colubriformis* larvae of sheep origin on day 0. On day 7, the gerbils are weighed and treatment initiated. Test compounds are administered by gavage on the 7th day after treatment. The gerbils are sacrificed on the 11th day after treatment, and the remaining worms counted. The percent efficacy is calculated by comparing worm counts in treated animals with those from untreated infected controls using the following formula.

$$\frac{\text{Control mean} - \text{treated mean}}{\text{control mean}} \times 100 = \% \text{ Efficacy}$$

Three replicates per treatment are employed in these evaluations.

The data obtained are summarized in Table I.

Evaluation of test compounds for controlling *Psoroptes cuniculi* (Ear Mites)

On the day prior to test, or the morning of test, test compounds are dissolved in acetone and diluted to the desired concentrations. The concentration should be calculated so that 400 μL contains the amount to be placed on each filter paper. 400 μL of this solution is pipetted onto a top (3.7 cm dia) and bottom (3.5 cm dia) filter paper disc which is then placed on a ceramic plate to dry. [NOTE: This should be done under a hood.] There is a rough and smooth side to the filter paper. The test solution should be applied to the rough side which is placed up while drying. When dry, the two discs are placed in a Petri dish with the rough sides facing in separated by a small piece of stiff paper folded in the shape of a tent. Dishes are held at room temperature overnight, if done the day before the test. A standard at 0.01, 0.1 and 1.0 μL/cm$^2$ is run in each test.

Scab (containing mites) is collected from the ears of infested rabbits the morning of the test. This material is placed in a large Petri dish under an illuminated magnifier. Mites crawl out of the scab and are easily collected on the point of a dissecting needle or one prong of a pair of fine forceps. The top filter paper in each dish is removed and 12 mites are placed on the bottom disk and the top paper replaced. Before replacing the top of the Petri dish the rim of the dish is smeared with Vaseline to trap any escaping mites.

For evaluation tests there are generally 4 replicates of each dose which are counted, 2 at 4 hours and 2 at 24 hours.

After mites are added to the dishes, the dishes in each replicate are placed in a tray which is then placed in a plastic bag with several wet towels and held at room temperature.

After 4 or 24 hours, dishes are examined under a dissecting scope as follows
1. Open dish carefully, remove top filter paper and save.
2. Draw a small circle approximately ½ cm in diameter on bottom filter paper using a soft pencil.
3. Using a disposable pipette, gently wet the area in and around the circle.
4. Transfer all mites from the dish into this circle. Look carefully—on cover, top filter paper and under bottom paper for mites.
5. Count and record the number of mites in the circle.
6. Replace the top cover and set the dish aside.
7. A minimum of 15 minutes later, count the mites remaining in the circle (these are dead mites).
8. Calculate and record the number of live mites.
9. Calculate percent efficacy as follows:

$$\frac{\text{Total of Dead mites}}{\text{Total number of mites}} \times 100 = \% \text{ Efficacy}$$

The data obtained are summarized in Table I.

Evaluation of test compounds for controlling *Musca domestica*

In this test system, newly emerged housefly larvae are grown on an undefined medium of fermented whole milk and dried beef blood. Test compounds are added to the milk and activity is determined by the failure of larvae to pupate.

The test is run in 1 oz plastic medicine cups. Paper toweling (Scott C-Fold towels, 150) is cut in pieces approximately 3.5×10 cm. Three of these pieces are folded accordion style and placed in each paper cup. Twenty-four hours before the initiation of the test, ½ gallon of whole milk is divided into 5 1-liter beakers and placed in an incubator at 39° C. The morning of the test, the fermented milk is removed from the incubator, stirred and poured into small beakers (100 mL each). The 1 to 2 g of dried beef blood is added to each beaker with stirring to distribute the blood and incubated.

Doses of test compounds are calculated so that 0.1 mL contains the amount of test compound to be added to 100 mL of milk. Compounds should be dissolved in acetone. 100 µL of acetone is added to each control beaker.

Each beaker is removed from incubator and placed on a magnetic stirrer. The test compound is added and throughly mixed. Then 20 mL portions are removed and added to labelled test cups (4 reps/treatment). Using a fine paint brush, 20 larvae are transferred into each cup which is then sealed in a plastic bag with a few pinholes in it. Bags containing cups are placed on a flat tray and placed in a 27° C. incubator for one week.

Trays are removed from incubator and the number of pupae in each bag recorded. The paper toweling is removed and examined closely for any pupae that have remained in the cups. Most of the pupae will be loose in the bag. The percent efficacy is calculated as follows:

$$\frac{\text{Number of pupae from 4 treatment cups}}{\text{Number of cups/treatment} \times 20} \times 100$$

The final results expressed as percent inhibition of pupation are corrected for control mortality by using Abbott's formula. Data obtained are summarized in Table I.

TABLE I

| | Evaluation Of The Antiparasitic Activity Of Test Compounds | | | | | | | | | |
|---|---|---|---|---|---|---|---|---|---|---|
| | T. colubriformis (mg/kg) | | | | P. cuniculi (micrograms/cm$^2$) | | | | M. domestica (ppm) | |
| Test Compound | 0.125 | 0.0625 | 0.0313 | 0.0156 | 4.0 | 1.0 | 0.1 | 0.01 | 10 | 1.0 |
| 13-Fluoro-23-(O-methyl-oxime)-LL-F28249alpha | 100 | 100 | 83 | 66 | 100 | 100 | 100 | 96 | 100 | 62 |
| 13-Fluoro-5-(formyloxy)-23-(O-methyloxime)-LL-F28249alpha | 100 | 86 | 82 | — | 100 | 100 | 100 | 38 | — | — |
| 26,27-Epoxy-13-fluoro-23-(O-methyloxime)-LL-F28249alpha | 100 | 100 | 100 | 98 | 100 | 100 | 100 | 7 | 79 | — |
| 5-(Dichloroacetoxy)-13-fluoro-23-(O-methyl-oxime)-LL-F28249alpha | 100 | 83 | 59 | — | 100 | 100 | 100 | 57 | 15 | — |
| 13-Fluoro-23-(O-methyl-oxime)-5-(trichloro-acetoxy)-LL-F28249alpha | 99 | 77 | 17 | — | 100 | 100 | 100 | 79 | — | — |

EXAMPLE 19

Evaluation Of The Insecticidal And Acaricidal Activity of Test Compounds

In the following evaluations, test solutions are prepared by dissolving the test compound in a 35% acetone in water mixture to a concentration of 10,000 ppm. Subsequent dilutions are made with water as needed.

*Heliothis virescens*, egg, tobacco budworm

A young cotton leaf about 6–7 cm long is dipped in the test solution with agitation for 3 seconds. Eggs are collected on a cheesecloth and the cheesecloth is cut into 10–20 mm squares containing about 50–100 eggs each (6–30 hours old). A square of cheesecloth with eggs is also dipped in the test solution and placed on the treated leaf. The combination is placed in a hood to dry, then placed in an 8 oz paper cup, into which a 5 cm length of damp dental wick has been placed. A clear plastic lid is put on the top of the cup and the treatments are held for 3 days before mortality counts are made.

*Heliothis virescens*, third-instar, tobacco budworm

Cotton cotyledons are dipped in the test solution and allowed to dry in a hood. When dry, each is cut into quarters and 10 sections are placed, individually, into 30 mL plastic medicine cups containing a 5-7 mm long piece of damp dental wick. One third-instar caterpillar is added to each cup, and a cardboard lid placed on the cup. Treatments are maintained for 3 days before mortality counts and estimates of reduction in feeding damage are made.

*Spondoptera eridania*, third-instar larvae, Southern armyworm

A Sieva lima bean leaf expanded to 7-8 cm in length is dipped in the test solution with agitation for 3 seconds and placed in a hood to dry. The leaf is then placed in a 100×10 mm petri dish containing a damp filter paper on the bottom and 10 third instar caterpillars. Observations of mortality, reduced feeding, or any interference with normal moulting are made at 3 days and 5 days.

*Aphis fabae*, mixed instar, bean aphid

Pots containing single nasturtium plants (Tropaeolum sp.) about 5 cm tall, are infested with about 100-200 aphids 1 day before the test. Each pot is sprayed with the test solution for 2 revolutions of a 4 rpm turn-table in a hood, using a #154 DeVilbiss atomizer. The spray tip is held about 15 cm from the plant, and the spray directed so as to give complete coverage of the plants and the aphids. The sprayed pots are set on their sides on white enamel trays and held for 2 days, following which mortality estimates are made.

*Empoasca abrupta*, adults, western potato leafhopper

A sieva lima bean leaf about 5 cm long is dipped in the test solution for 3 seconds with agitation and placed in a hood to dry. The leaf is placed in a 100×10 mm petri dish containing a moist filter paper on the bottom.

About 10 adult leafhoppers are added to each dish, and the treatments are kept for 3 days before mortality counts are made.

*Tetranychus urticae* (P-resistant strain) 2-spotted spider mite

Sieva lima bean plants with primary leaves expanded to 7-8 cm are selected and cut back to one plant per pot. A small piece is cut from a leaf taken from the main colony of mites and placed on each leaf of the test plants. This is done about 2 hours before treatment to allow the mites to move over to the test plant and to lay eggs. The size of the cut piece is varied to obtain about 100 mites per leaf. At the time of the treatment, the piece of leaf used to transfer the mites is removed and discarded. The mite-infested plants are dipped in the test solution for 3 seconds with agitation and set in the hood to dry. Plants are kept for 2 days before estimates of adult kill are made using the first leaf. The second leaf is kept on the plant for another 5 days before observations are made of the kill of eggs and/or newly emerged nymphs.

| Rating Scale | |
|---|---|
| 0 = no effect | 5 = 56–65% kill |
| 1 = 10–25% kill | 6 = 66–75% kill |
| 2 = 26–35% kill | 7 = 76–85% kill |
| 3 = 36–45% kill | 8 = 86–99% kill |
| 4 = 46–55% kill | 9 = 100% kill |

The data obtained are summarized in Table II.

TABLE II

| Evaluation Of The Insecticidal And Acaricidal Activity Of Test Compounds | | | | | | | | | | | | | |
|---|---|---|---|---|---|---|---|---|---|---|---|---|---|
| | Tobacco Budworm | | | | Southern Armyworm | | | Bean Aphid (ppm) | Leaf-hopper (ppm) | | P-resistant Mites (ppm) | | |
| | egg (ppm) | | 3rd instar (ppm) | | Day 3 (ppm) | | Day 5 (ppm) | | | | | | |
| Test Compound | 100 | 10 | 100 | 10 | 10 | 1 | 10 | 10 | 100 | 10 | 1000 | 100 | 10 |
| 13-Fluoro-23-(O-methyloxime)-LL-F28249alpha | 8 | 0 | 9 | 9 | 9 | 4 | 9 | 7 | 7 | 6 | 9 | 5 | 8 |
| 5-(Dichloroacetoxy)-13-fluoro-23-(O-methyloxime)-LL-F28249alpha | 0 | 0 | 9 | 9 | 9 | 5 | 9 | 9 | 7 | 0 | 9 | 9 | 8 |
| 13-Fluoro-23-(O-methyloxime)-5-(trichloroacetoxy)-LL-F28249alpha | 8 | 0 | 9 | 9 | 4 | 3 | 9 | 9 | 0 | 0 | 9 | 9 | 8 |
| 13-Fluoro-5-(formyloxy)-23-(O-methyloxime)-LL-F28249alpha | 0 | 0 | 9 | 8 | 9 | 1 | 9 | 9 | 0 | 0 | 9 | 9 | 8 |

What is claimed is:
1. A compound having the structural formula:

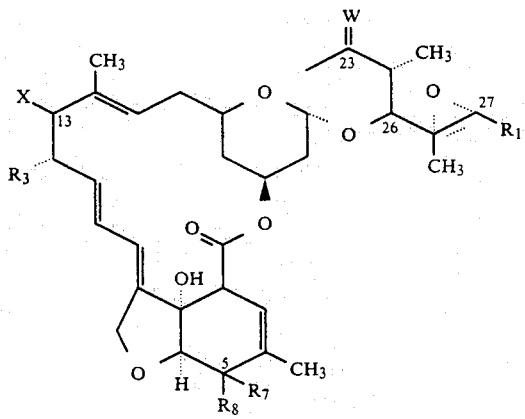

wherein
R₁ is methyl, ethyl or isopropyl;
R₇ is hydrogen and R₈ is OR₂; or when taken together with the carbon atom to which they are attached R₇ and R₈ represent C=O;
R₂ is hydrogen, C₁-C₄ alkyl, or

R₄ is hydrogen, C₁-C₄ alkyl, C₁-C₄ haloalkyl, C₁-C₄ alkoxy, phenoxy, C₁-C₄ alkoxymethyl, phenoxymethyl, or phenyl optionally substituted with 1 nitro, 1-3 halogens, 1-3 C₁-C₄ alkyl, or 1-3 C₁-C₄ alkoxy;
R₃ is hydrogen, methyl or ethyl;
X is fluorine, bromine, chlorine or iodine;
W is N=Y;
Y is OR₅ or NHR₆;
R₅ is C₁-C₄ alkyl or C₁-C₄ acyl;
R₆ is C₁-C₄ acyl; and
the dotted triangular figure with oxygen at C₂₆-C₂₇ indicates that there is present either a double bond or an epoxide.

2. The compound according to claim 1, wherein R₁ is isopropyl;
R₇ is hydrogen and R₈ is OR₂;
R₂ is hydrogen, C₁-C₄ alkyl, or

R₄ is hydrogen, methyl, chloromethyl, dichloromethyl, trichloromethyl, or methoxymethyl;
R₃ is methyl;
X is fluorine;
W is N=Y;
Y is OR₅; and
R₅ is C₁-C₄ alkyl.

3. The compound according to claim 2, wherein R₂ is hydrogen; R₅ is methyl; and the dotted triangular figure with oxygen at C₂₆-C₂₇ indicates that there is present a double bond.

4. The compound according to claim 3, wherein the dotted triangular figure with oxygen at C₂₆-C₂₇ indicates that there is present an epoxide.

5. The compound according to claim 3, wherein R₂ is

and
R₄ is hydrogen.

6. The compound according to claim 5, wherein R₄ is dichloromethyl.

7. The compound according to claim 5, wherein R₄ is trichloromethyl.

8. A method for the prevention, treatment or control of an endoparasitic or ectoparasitic infection in a warm-blooded animal which comprises administering to the animal an endo- or ectoparasiticidally effective amount of a compound having the structural formula:

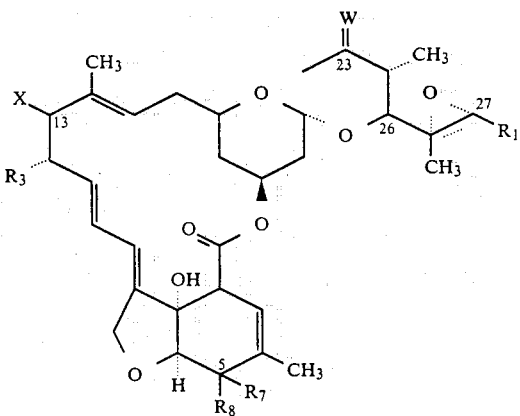

wherein
R₁ is methyl, ethyl or isopropyl;
R₇ is hydrogen and R₈ is OR₂, or when taken together with the carbon atom to which they are attached R₇ and R₈ represent C=O;
R₂ is hydrogen, C₁-C₄ alkyl, or

R₄ is hydrogen, C₁-C₄ alkyl, C₁-C₄ haloalkyl, C₁-C₄ alkoxy, phenoxy, C₁-C₄ alkoxymethyl, phenoxymethyl, or phenyl optionally substituted with 1 nitro, 1-3 halogens, 1-3 C₁-C₄ alkyl, or 1-3 C₁-C₄ alkoxy;
R₃ is hydrogen, methyl or ethyl;
X is fluorine, bromine, chlorine or iodine;
W is N=Y;
Y is OR₅ or NHR₆;
R₅ is C₁-C₄ alkyl or C₁-C₄ acyl;
R₆ is C₁-C₄ acyl; and
the dotted triangular figure with oxygen at the C₂₆-C₂₇ indicates that there is present either a double bond or an epoxide.

9. The method according to claim 8, wherein said compound has the structural formula as described in claim 9 and
R₁ is isopropyl;
R₇ is hydrogen; R₈ is OR₂;
R₂ is hydrogen, C₁-C₄ alkyl, or

R$_4$ is hydrogen, methyl, chloromethyl, dichloromethyl, trichloromethyl, or methoxymethyl;
R$_3$ is methyl;
X is fluorine;
W is N=Y;
Y is OR$_5$; and
R$_5$ is C$_1$-C$_4$ alkyl.

10. A method for protecting crops, trees, shrubs, stored grain or ornamental plants from attack by an insect, acarid or nematode which comprises applying to said crops, trees, shrubs, stored grain or ornamental plants an insecticidally, acaricidally or nematocially effective amount of a compound having the structural formula:

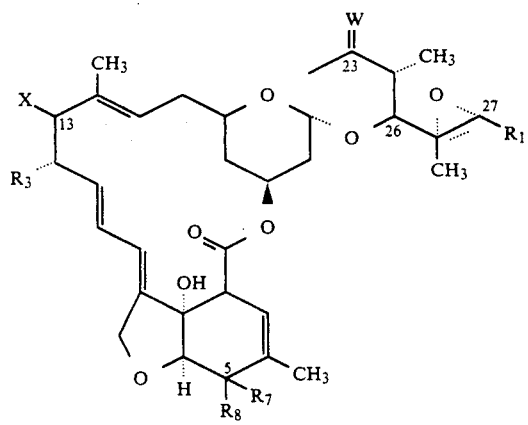

wherein
R$_1$ is methyl, ethyl or isopropyl;
R$_7$ is hydrogen and R$_8$ is OR$_2$, or when taken together with the carbon atom to which they are attached R$_7$ and R$_8$ represent C=O;
R$_2$ is hydrogen, C$_1$-C$_4$ alkyl, or

R$_4$ is hydrogen, C$_1$-C$_4$ alkyl, C$_1$-C$_4$ haloalkyl, C$_1$-C$_4$ alkoxy, phenoxy, C$_1$-C$_4$ alkoxymethyl, phenoxymethyl, or phenyl optionally substituted with 1 nitro, 1-3 halogens, 1-3 C$_1$-C$_4$ alkyl, or 1-3 C$_1$-C$_4$ alkoxy;
R$_3$ is hydrogen, methyl or ethyl;
X is fluorine, bromine, chlorine or iodine;
W is N=Y;
Y is OR$_5$ or NHR$_6$;
R$_5$ is C$_1$-C$_4$ alkyl or C$_1$-C$_4$ acyl;
R$_6$ is C$_1$-C$_4$ acyl; and
the dotted triangular figure with oxygen at C$_{26}$-C$_{27}$ indicates that there is present either a double bond or an epoxide.

11. The method according to claim 10, wherein the compound has the structural formula as described in claim 11 and
R$_1$ is isopropyl;
R$_7$ is hydrogen; R$_8$ is OR$_2$;
R$_2$ is hydrogen, C$_1$-C$_4$ alkyl, or

R$_4$ is hydrogen, methyl, chloromethyl, dichloromethyl, trichloromethyl, or methoxymethyl;
R$_3$ is methyl;
X is fluorine;
W is N=Y;
Y is OR$_5$; and
R$_5$ is C$_1$-C$_4$ alkyl.

12. The method according to claim 10, wherein the insect is a housefly.

13. A composition for controlling endo- or ectoparasites, insects, acarids nematodes comprising an agronomically acceptable carrier containing a prophylactically, therapeutically, pharmaceutically or insecticidally effective amount of a compound having the structural formula:

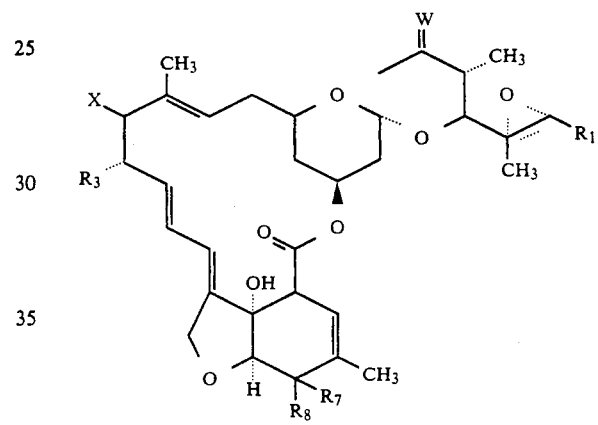

wherein
R$_1$ is methyl, ethyl or isopropyl;
R$_7$ is hydrogen and R$_8$ is OR$_2$, or when taken together with the carbon atom to which they are attached R$_7$ and R$_8$ represent C=O;
R$_2$ is hydrogen, C$_1$-C$_4$ alkyl, or

R$_4$ is hydrogen, C$_1$-C$_4$ alkyl, C$_1$-C$_4$ haloalkyl, C$_1$-C$_4$ alkoxy, phenoxy, C$_1$-C$_4$ alkoxymethyl, phenoxymethyl, or phenyl optionally substituted with 1 nitro, 1-3 halogens, 1-3 C$_1$-C$_4$ alkyl, or 1-3 C$_1$-C$_4$ alkoxy;
R$_3$ is hydrogen, methyl or ethyl;
X is fluorine, bromine, chlorine or iodine;
W is N=Y;
Y is OR$_5$ or NHR$_6$;
R$_5$ is C$_1$-C$_4$ alkyl or C$_1$-C$_4$ acyl;
R$_6$ is C$_1$-C$_4$ acyl; and
the dotted triangular figure with oxygen at C$_{26}$-C$_{27}$ indicates that there is present either a double bond or an epoxide.

* * * * *

UNITED STATES PATENT AND TRADEMARK OFFICE
CERTIFICATE OF CORRECTION

PATENT NO. : 5,030,650

DATED : July 9, 1991

INVENTOR(S) : Brian L. Buckwalter; Shin-Shyong Tseng

It is certified that error appears in the above-identified patent and that said Letters Patent is hereby corrected as shown below:

In col. 1, lines 30-35; cols. 3-12, Flow Diagrams I-V; claim 1, col. 23, lines 3-8; claim 8, col. 24, lines 20-23; claim 10, col. 25, lines 22-25; and claim 13, col. 26, lines 25-28, that portion of the twenty-two formulas reading:

In col. 1, line 65; col. 2, line 19; claim 1, col. 23, line 37; claim 2, col. 23, line 57; claim 8, col. 24, line 55; claim 9, col. 25, line 10; claim 10, col. 25, line 55; claim 11, col. 26, line 12; and claim 13, col. 26, line 58, the configuration "N=Y" in nine occurrences should read --N-Y--.

In claim 9, col. 24, line 65, the reference to "claim 9" should read --claim 8--.

In claim 10, col. 25, line 17, the word "nematocially" should read --nematocidally--.

In claim 11, col. 25, line 64, the reference to "claim 11" should read --claim 10--.

UNITED STATES PATENT AND TRADEMARK OFFICE
CERTIFICATE OF CORRECTION

PATENT NO. : 5,030,650

DATED : July 9, 1991

INVENTOR(S) : Brian L. Buckwalter; Shin-Shyong Tseng

It is certified that error appears in the above-identified patent and that said Letters Patent is hereby corrected as shown below:

In claim 13, col. 26, line 18, the phrase "acarids mematodes" should read --acarids or nematodes--.

Signed and Sealed this

Fourth Day of May, 1993

Attest:

MICHAEL K. KIRK

*Attesting Officer*   *Acting Commissioner of Patents and Trademarks*